(12) United States Patent
Hosoi

(10) Patent No.: US 7,216,984 B2
(45) Date of Patent: May 15, 2007

(54) OPTOMETRIC APPARATUS

(75) Inventor: Yoshinobu Hosoi, Gamagori (JP)

(73) Assignee: Nidek Co., Ltd., Gamagori-shi (JP)

( * ) Notice: Subject to any disclaimer, the term of this patent is extended or adjusted under 35 U.S.C. 154(b) by 418 days.

(21) Appl. No.: 10/624,641

(22) Filed: Jul. 23, 2003

(65) Prior Publication Data

US 2005/0105050 A1    May 19, 2005

(30) Foreign Application Priority Data

Jul. 31, 2002    (JP) .............................. 2002-224279

(51) Int. Cl.
*A61B 3/02* (2006.01)
(52) U.S. Cl. ............... 351/237; 351/222; 351/205; 351/221; 351/211; 351/243; 351/246; 351/218; 351/242
(58) Field of Classification Search ......... 351/200–247
See application file for complete search history.

(56) References Cited

U.S. PATENT DOCUMENTS 2,707,901 A * 5/1955 Thorburn .................. 351/218
3,001,442 A * 9/1961 Brock ...................... 351/246
4,861,154 A * 8/1989 Sherwin et al. ............. 351/205
4,861,156 A * 8/1989 Terry ........................ 351/243
4,953,968 A * 9/1990 Sherwin et al. ............. 351/211
5,297,559 A * 3/1994 Severns ..................... 600/558
5,640,221 A * 6/1997 Ishikawa et al. ............ 351/221
5,805,268 A * 9/1998 Hosoi et al. ................ 351/211
5,856,861 A * 1/1999 Hosoi et al. ................ 351/237
5,859,688 A * 1/1999 Hosoi et al. ................ 351/237
5,929,971 A * 7/1999 Hosoi et al. ................ 351/237
5,997,142 A * 12/1999 Nakagawa .................. 351/221
2003/0081175 A1   5/2003 Hosoi et al.

FOREIGN PATENT DOCUMENTS

JP    A 10-179518    7/1998

* cited by examiner

*Primary Examiner*—Brian L Casler
*Assistant Examiner*—Sanjay Cattungal
(74) *Attorney, Agent, or Firm*—Oliff & Berridge PLC

(57) ABSTRACT

An optometric apparatus for a subjective examination of a visual function of an eye of an examinee includes a pair of right and left lens chamber units, each including, a test window and a rotating disk on which a plurality of optical elements are mounted in a circumferential arrangement to be changeably placed in the test window, the optical elements including a green filter and an aperture.

9 Claims, 5 Drawing Sheets

① : PRESENT GREEN OPTOTYPE

② : NO OPTOTYPE

③ : PRESENT BOTH RED AND GREEN OPTOTYPES

OPTOMETRIC APPARATUS

BACKGROUND OF THE INVENTION

1. Field of the Invention

The present invention relates to an optometric apparatus for a subjective examination of a visual function (a visual acuity, etc.) of an eye of an examinee.

2. Description of Related Art

There is a red/green test (R/G test) as one of subjective examinations which are performed for prescribing the powers of spectacle lenses or contact lenses. This R/G test uses a red optotype and a green optotype having a red and green backgrounds adjacently placed, on each of which black figure targets and black character targets, identical between the red and green optotypes, are drawn or printed. This R/G test is performed for a check on final overcorrection or for a preliminary test of an astigmatism examination using a cross-cylinder. In this R/G test, the red and green optotypes are concurrently presented to an examinee (an examinee's eye) and the examinee is asked to tell a difference in vision between the optotypes, in other words, about which optotype is more clearly visible.

The R/G test, meanwhile, is regarded as effective for the eyes having little or small amplitude of accommodation (i.e., focusing ability of a crystalline lens), whereas the test would not be performed correctly on the eyes having a normal or large amplitude of accommodation because such eyes attempt to automatically accommodate during the test. Hence, Japanese patent unexamined publication No. Hei 10-179618 proposed a method in which a green optotype is presented to an examinee for a predetermined time or a green optotype is presented in a blinking state for a predetermined time and then the green optotype and a red optotype are simultaneously presented, and such steps are repeated while prompting an examinee to compare and respond about a difference in vision between the optotypes. According to this method, it is considered that the R/G test can efficiently be utilized when the automatic accommodation of the examinee is restrained as much as possible.

However, the test method disclosed in the above publication includes the particular steps of presenting the green optotype to the examinee for a predetermined time and then concurrently presenting the green and red optotypes. Thus, such test method could not be achieved by use of general-purpose optotype presenting devices commercially available at present.

SUMMARY OF THE INVENTION

The present invention has been made in view of the above circumstances and has an object to overcome the above problems and to provide an optometric apparatus capable of performing a R/G test by a method using general-purpose red and green optotypes which are commercially available at present, in which only the green optotype is presented before the green and red optotypes are simultaneously presented.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometric apparatus for a subjective examination of a visual function of an eye of an examinee, the apparatus including: a pair of right and left lens chamber units, each including, a test window; and a rotating disk on which a plurality of optical elements are mounted in a circumferential arrangement to be changeably placed in the test window, the optical elements including a green filter and an aperture.

According to another aspect of the invention, there is provided an optometric apparatus for a subjective examination of a visual function of an eye of an examinee, the apparatus including: a pair of right and left lens chamber units, each including, a test window; and a rotating disk on which a plurality of optical elements are mounted in a circumferential arrangement to be changeably placed in the test window, the optical elements including a green filter and an aperture; and control means having a test program including the following steps: a first step of placing the green filter in the test window for a first predetermined time; a second step of placing the aperture in the test window after the first step, for a second predetermined time; and a third step of repeating the first and second steps a predetermined number of times.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
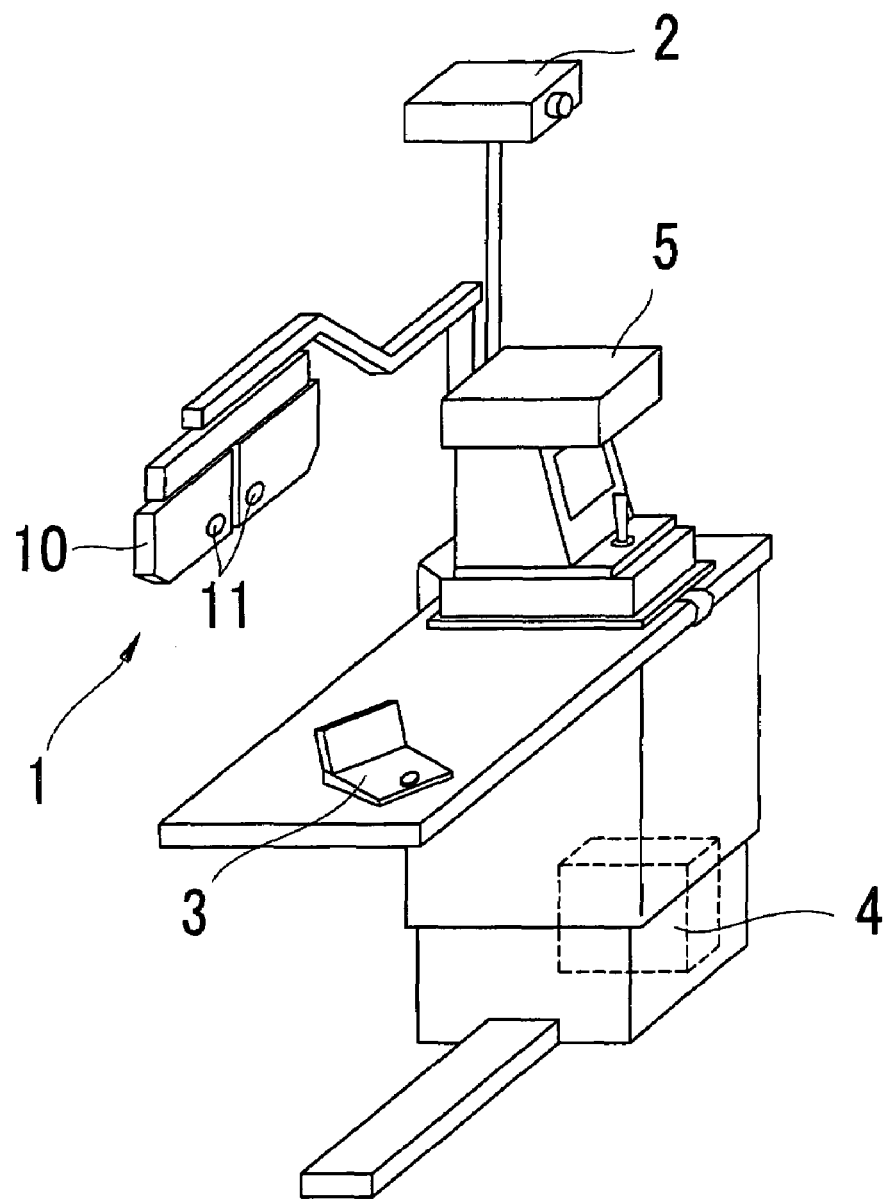
FIG. 1 is a schematic external view of an optometric apparatus in an embodiment.
Figure 2:
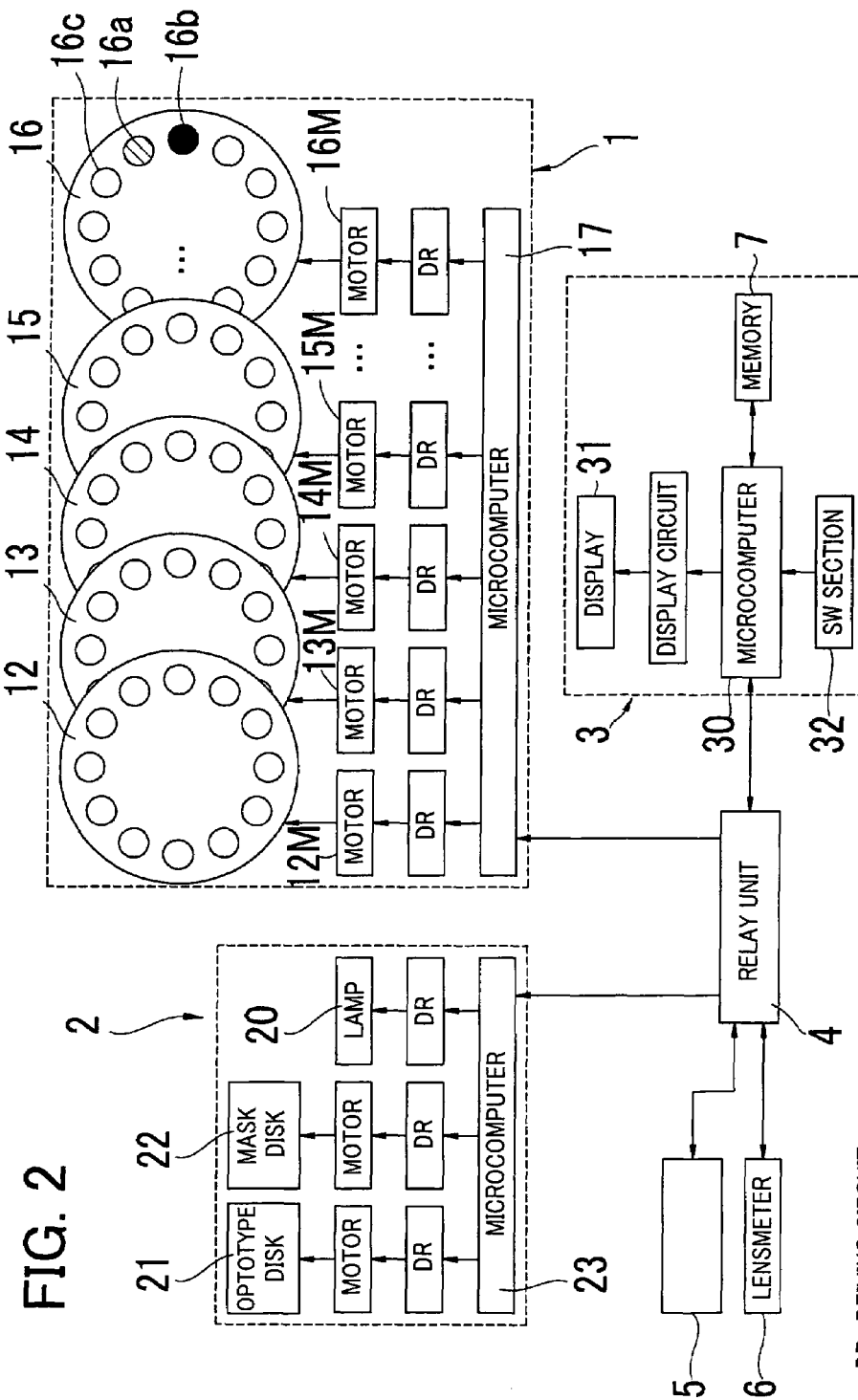
FIG. 2 is a schematic structural view of a main part including a control system.

A detailed description of a preferred embodiment of an optometric apparatus embodying the present invention will now be given referring to the accompanying drawings. FIG. 1 is a schematic external view of the optometric apparatus in the present embodiment. FIG. 2 is a schematic structural view of a main part including a control system.

Numeral 1 is a main unit of the optometric apparatus, including a pair of right and left lens chamber units 10, each housing rotatable lens disks. On each lens disk, many optical elements are mounted in a circumferentially-spaced-apart arrangement. The lens disks include a low-power spherical lens disk 12, a high-power spherical lens disk 13, an astigmatic lens disk 14, a lens disk 15 having a cross-cylinder, and an auxiliary lens disk 16 having a green filter 16a, a shielding plate 16b, and others. Each disk has an aperture (e.g., as shown by the numeral 16c in the auxiliary lens disk 16). The green filter 16a, the shielding plate 16b, and the aperture 16c are used for a R/G test mentioned later and therefore preferably mounted adjacent to each other on the auxiliary lens disk 16. Specifically, as shown in FIG. 2, the shielding plate 16b and the aperture 16c are positioned on both sides of the green filter 16a. Each disk is rotated by a corresponding one of motors 12M to 16M to changeably place a desired corrective optical system (optical elements) in a test window 11.

It is to be noted that the aperture in the present embodiment may include, besides a simple aperture (hole), the case where an optical element having little refractive power such as a lens of 0 D (diopter) is set in the aperture. In the present embodiment, the green filter 16a and the shielding plate 16b are mounted on the auxiliary lens disk 16, but not limited thereto. As an alternative design, the shielding plate may be mounted on a different disk from the disk having the green filter. In this case, the shielding plate may be set on the disk to be unused for the R/G test (i.e., the disk on which corrective lenses and the like are not mounted).

Numeral 2 is an optotype presenting device for presenting examination optotypes. This device 2 is constructed such that a lamp 20 is turned on and an optotype disk 21 and a mask disk 22 are rotated to project a desired optotype (target) on a screen not shown placed forward of an examinee's eye. The optotype presenting device 2 in the present embodiment is a projection type, but it is not limited thereto. For example, the conventionally used optotype presenting device, such as a small-footprint type (which uses a concave mirror and many reflection mirrors), a stationary type (which illuminates optotypes from behind), etc., may also be used as long as it has the optotypes for a R/G test.

Numeral 3 is a controller to be used for operating the main unit 1 and the optotype presenting device 2. This controller 3 is provided with a display 31, a switch section 32, and others. A switch signal from the controller 3 is transmitted to the main unit 1 and the optotype presenting device 2, respectively, through a relay unit 4. In accordance with the received signal, a microcomputer 17 controls motions of each lens disk and optotype disk.

Numeral 5 is an objective refractive power measurement device for objectively measuring the refractive power of the eye by projecting an index for measurement onto the fundus of the eye and detecting an image of the projected index by light receiving means. Numeral 6 is a lensmeter for measuring optical properties of spectacle lenses. The data on objective measurement values and spectacle lens values from the measurement device 5 and the lensmeter 6 respectively is transmitted to the controller 3 through the relay unit 4 and stored in a memory 7.

Figure 3:
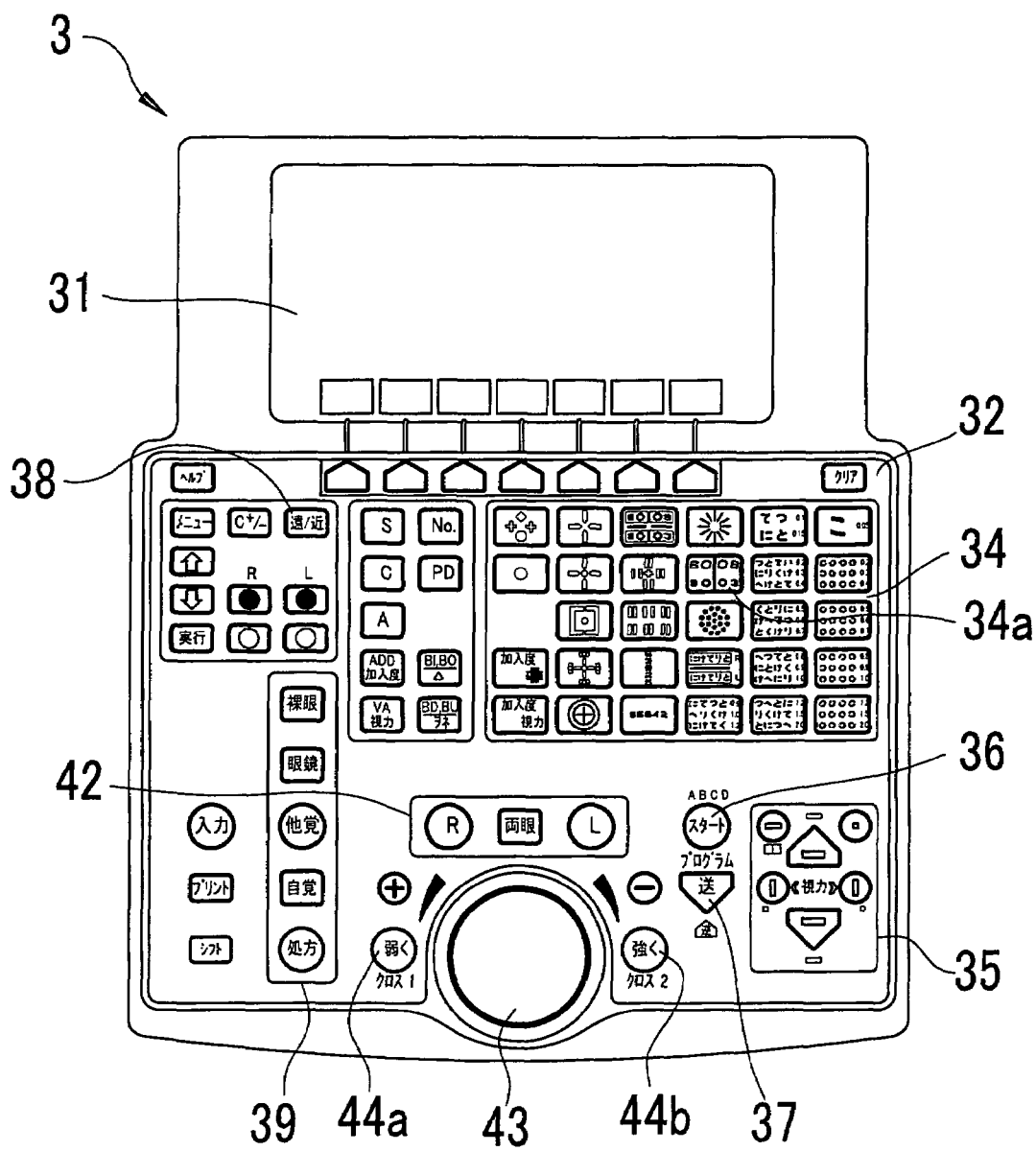
FIG. 3 is a plane view of a controller.

FIG. 3 is a plane view of the controller 3. Numeral 31 is a liquid crystal display for displaying optometry information. Numeral 32 is a switch section including a group of optotype switches 34, a group of mask switches 36, a start switch 36 for a programmed optometry and an advance switch 37, a group of switches 38 for specifying a mode to change measurement data (S, C, A, etc.), a group of switches 39 for specifying input data, a group of switches 42 for specifying an eye to be examined, a dial switch 43 to be used in inputting a change in the measured values and numbers, switches 44b and 44a for changing a cross-cylinder to another one having a higher or lower power, and so on.

The operation of the apparatus having the above structure is explained below. The explanation is herein made with a focus on the R/G test.

To perform the subjective examination, there are used objective data obtained by the objective refractive power measurement device 5 and spectacle lens data (i.e., power data on a previous spectacle lens) obtained by the lensmeter 6. Optical elements of the corrective optical system initialized based on the data are placed in the test window 11, thus enabling an efficient subjective examination.

When the one of the switch group 42 is pressed to specify one of right and left eyes, the shielding plate 16b of the auxiliary lens disk 16 for the unselected eye is placed in the test window 11 to be unused. The examiner pushes the switches of the optotype switch group 34 to cause the optotype presenting device 2 to display a necessary optotype for the examination. In the test window 11 to be used for the examination, the corrective optical system for sphere and astigmatism are changeably placed by the switch group 38, the dial switch 43, and the switches 44a and 44b.

Figure 6:
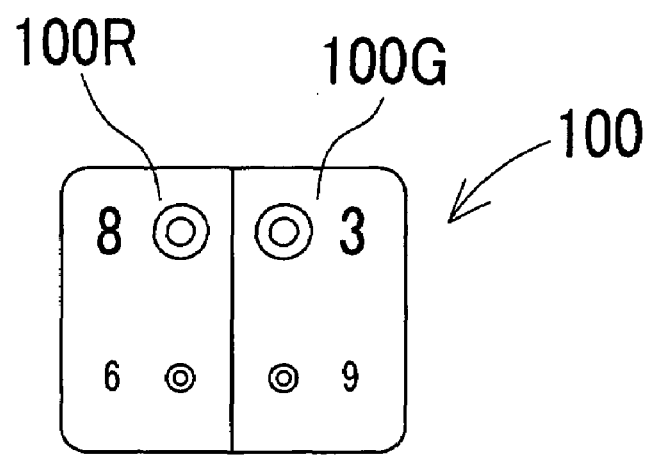
FIG. 6 is a front view of optotypes for a R/G test.

To start the R/G test for checks on overcorrection and others, the examiner presses the R/G test switch 34a of the optotype switch group 34. The microcomputer 80 sends a command signal for presentation of the R/G test optotype 100 shown in FIG. 6 to the optotype presenting device 2. When the switch 34a is pressed, the microcomputer 30 executes the R/G test program to add the green filter 16a to the test window 11 for the eye under examination and transmits a command signal thereon (this program having been stored in the memory 7).

The microcomputer 17 causes the motor 16M to rotate the auxiliary lens disk 16 in response to the command signal based on the R/G test program, thereby placing the green filter 16a in the test window 11 for the eye under examination. When the examinee (examinee's eye) looks at the R/G test optotype 100 presented forward of the eye through the test window 11, only the green optotype 100G is visible (the red optotype 100R is invisible). The examiner prompts the examinee to gaze at the green optotype 100G.

After a lapse of a predetermined time (e.g., 4 seconds) from when the green filter 16a is set in the test window 11, subsequently, the microcomputer 17 controls to rotate the auxiliary lens disk 16 to place the aperture 16c in the test window 11. When the aperture 16c is placed in the test window 11, the examinee can simultaneously look at both the red optotype 100R and the green optotype 100G presented forward of the examinee by the presenting device 2.

Furthermore, after a lapse of a predetermined time (e.g., 1 second) from when the aperture 16c is placed in the test window 11, the microcomputer 17 controls to rotate the auxiliary lens disk 16 to set the green filter 16a again in the test window 11 so that only the green optotype 100G is presented. While such control is repeated, the R/G test is performed; specifically, the examiner asks the examinee to tell which one of the red and green optotypes is more clearly visible, black targets on a red background or black targets on a green background.

In this way, in the R/G test in the present embodiment, the operation of presenting only the green optotype 100G for the first predetermined time and then simultaneously presenting the red optotype 100R and the green optotype 100G for the second predetermined time is repeated a predetermined number of times.

Specifically, only the green optotype is first presented to the examinee (the examinee's eye) who is prompted to gaze it so that green light is focused on the retina. After several seconds in this state, the red optotype is additionally presented. Since the focal point of the green light is closer to the retina than that of the red light, the green optotype will be clearly visible. At this time, the eye (crystalline lens) attempts to accommodate to focus on the red optotype, but the red optotype is presented only for a short time (about 1 second) and therefore becomes invisible before the eye fully focuses on the red optotype. Accordingly, the eye focuses on the green optotype again. This operation is repeated while prompting the examinee to compare a difference in vision between the optotypes. Thus, the automatic accommodation of the examinee (the examinee's eye), namely, the focusing ability of the crystalline lens can be restrained as much as possible. This makes it possible to perform the R/G test with high accuracy and therefore effectively utilize the test result.

Heretofore, such R/G test has been difficult to perform by use of general-purpose optotype presenting devices commercially available at present. Using the optometric apparatus in the present embodiment, however, the R/G test can be carried out by use of the general-purpose optotype presenting devices.

In the present embodiment, the presenting time of only the green optotype 100G is set at 4 seconds and the simultaneous presenting time of the red and green optotypes 100R and 100G is set at 1 second, but these times are not limited thereto. The former may be set at a time length considered as sufficient for the examinee to gaze only the green optotype 100G and the latter may be set at a time length allowing the red optotype 100R to become invisible before the examinee's eye comes into focus on the red optotype 100R after the green and red optotypes 100R and 100G are simultaneously presented.

Alternatively, the green optotype 100G may be presented intermittently, not continuously as described above, and, after a predetermined time, the red optotype 100R and the green optotype 100G are simultaneously presented. The method of executing the R/G test using such control is explained below as a second embodiment. It is to be noted that the optometric apparatus shown in FIGS. 1 to 3 is also used in the second embodiment. Herein, only the operation of the apparatus in the R/G test is described.

When the switch 34a is pressed, the microcomputer 30 transmits a command signal for presentation of the R/G test optotype to the optotype presenting apparatus 2 and further transmits a command signal based on the R/G test program to the main unit 1.

In response to the command signal, the microcomputer 17 controls to rotate the auxiliary lens disk 16 to alternately place the green filter 16a and the shielding plate 16b in the test window 11 for the eye under examination. As shown in FIG. 2, the green filter 16a and the shielding plate 16b are arranged adjacent to each other on the auxiliary lens disk 16, so that other optical elements and so on are not allowed to pass in front of the test window 11 when the green filter 16a and the shielding plate 16b are alternately placed in the test window 11. While such alternate placing is successively performed, the green optotype 100G presented forward of the examinee will be visible as if it blinks.

By presenting the green optotype 100G as if blinking, it is possible to make the green optotype 100G noticeable so that the examinee may easily gaze it. After presenting the green optotype 100G as if blinking for the predetermined time (a first predetermined time), the microcomputer 17 controls to place the aperture 16c in the test window 11 for another predetermined time (a second predetermined time), thereby concurrently presenting both the red optotype 100R and the green optotype 100G. The above operation is repeated a predetermined number of times and then the examinee is prompted to determine which optotype is more clearly visible.

Figure 4:
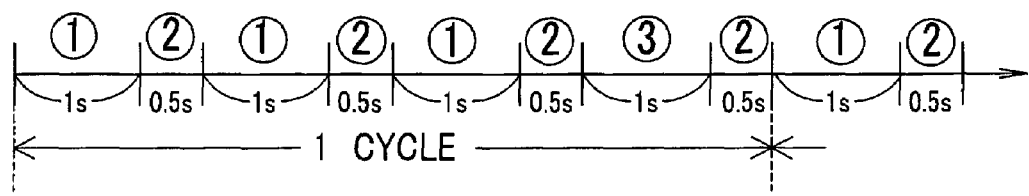
FIG. 4 is a time chart in control of rotating operation of auxiliary lens disks.

Such control of the rotating operation of the auxiliary lens disk 16 by the microcomputer 17 is shown in detail as a time chart in FIG. 4. In this chart, mark ① indicates that the green filter 16a is placed in the test window 11, mark ② indicates that the shielding plate 16b is placed in the test window 11, and mark ③ indicates that the aperture 16c is placed in the test window 11.

As shown in FIG. 4, the green filter 16a is placed in the test window 11 for 1 second, when only the green filter 100G is presented to the examinee. Thereafter, the shielding plate 16b is placed in the test window 11 for 0.5 second, when no optotype is presented to the examinee. In the test window 11, sequentially, the green filter 16a is placed again for 1 second and then the shielding plate 16b is placed for 0.5 second.

As above, the green filter 16a and the shielding plate 16b are alternately placed three times each and then the aperture 16c is set in the test window 11 for 1 second, when the red optotype 100R and the green optotype 100G are simultaneously presented to the examinee. This is regarded as one cycle. The microcomputer 17 thus controls the rotation of the auxiliary lens disk 16 to repeat this cycle until receives a command signal to advance the test step to next one.

It is to be noted that, in the second embodiment, the blinking presentation of the green optotype 100G is set to have a presenting (appearing) time of 1 second and a shielding (disappearing) time of 0.5 second, but not limited thereto. Those times may be set at different time lengths if only the green optotype 100G is made noticeable so that the examinee can gaze it. The blinking presenting time of the green optotype 100G is set at 4.5 seconds and the subsequent simultaneously presenting time of the red and green optotypes 100R and 100G is set at 1 second, but not limited thereto. The former may be set at a time length considered as sufficient for the examinee to gaze only the green optotype 100G and the latter may be set at a time length allowing the red optotype 100R to become invisible (disappear) before the examinee's eye fully focuses on the red optotype 100R after both optotypes are simultaneously presented.

In the above embodiments, the optometric apparatus adapted to electrically rotate the lens disks 12 to 16 is explained. Besides this type, the present invention can be applied to another type of optometric apparatus adapted to manually rotate those disks.

Moreover, when the test is performed by adding a lens of plus power (diopter) (e.g., +0.5 D) to the corrective optical system placed in the test window 11 so that the presented optotype gets intentionally blurred, the accommodation becomes hard to act. Thus, the R/G test can be conducted more accurately.

If the examinee's eye has astigmatism, the R/G test has to be performed before the examination on the astigmatic axis and astigmatic power in order to position a minimum circle of confusion on the retina of the examinee's eye. The present invention can be applied to such R/G test.

Figure 5:
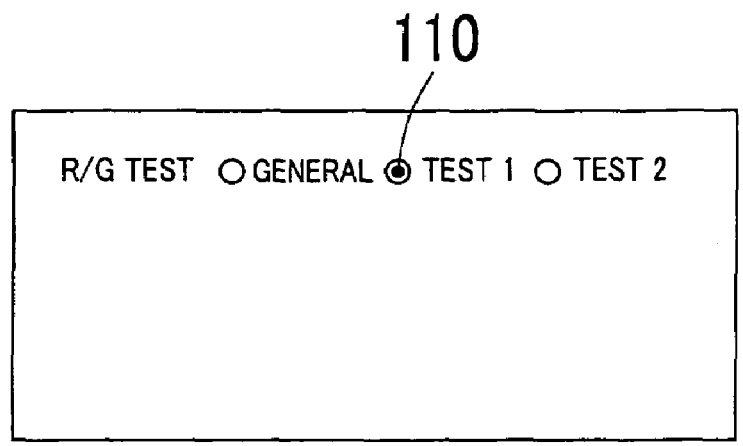
FIG. 5 is a view of a setting screen for selecting R/G tests.

Furthermore, it is also possible to selectively execute the R/G test method according to the present invention and the conventional R/G test method. This selection is made in the following manner. A menu switch on the controller 3 is pressed to display a parameter setting screen on the display 31. When an item of the R/G test is retrieved from among parameter setting options, a setting screen as shown in FIG. 5 is displayed on the display 31. In FIG. 5, a black circle 110 indicates a selected test method. The black circle 110 is shifted by operation of the dial switch 43. To perform the conventional R/G test in which the green filter 16a is not placed in the test window 11, an option "General" is selected. To perform the test method described first in which the green filter 16a is continuously placed in the test window 11, another option "Test 1" is selected. To perform the test method mentioned in the second embodiment in which the green filter 16a is intermittently placed in the test window 11, another option "Test 2" is selected. In this way, the control program to rotate the lens disk 16 can be changed according to the R/G test to be carried out. Thus, the conventional R/G test can also be performed.

It is to be noted that the colors of the green optotype and the red optotype in the above embodiments are determined based on that a difference in wavelength between the green light (short wavelengths) and the red light (long wavelengths) causes a difference in the focal points on the retina. However, any colors (similar colors to green, similar colors to red) may be used if only they have the focal points in front and rear of the retina respectively at almost equal distances in the case where white reference light (exactly, yellow light of about 590 nm) is focused on the retina. Furthermore, any green filter may be used if only having a wavelength property of making the green optotype easily visible and the red optotype hardly visible.

According to the present invention, as described above, the R/G test of the type which presents only the green optotype before simultaneously presenting the green optotype and the red optotype can be performed by use of general-purpose R/G test optotypes commercially available at present.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometric apparatus for a subjective examination of a visual function of an eye of an examinee, the apparatus including:
   a pair of right and left lens chamber units, each including,
      a test window; and
      a rotating disk on which a plurality of optical elements are mounted in a circumferential arrangement to be changeably placed in the test window, the optical elements including a green filter and an aperture;
   instruction means for generating a signal to instruct a start of a red/green test in which a red optotype and a green optotype are simultaneously presented to the examinee's eye; and
   control means for drivingly controlling the rotating disk in response to the signal from the instruction means to place the green filter in the test window for a first predetermined time and then place the aperture in the test window for a second predetermined time while the red optotype and the green optotype are simultaneously presented to the examinee's eye.

2. The optometric apparatus according to claim 1, wherein the rotating disk mounts thereon a shielding plate as one of the optical elements, the shielding plate being used for shielding the test window.

3. The optometric apparatus according to claim 2, wherein the control means drivingly controls the rotating disk in response to the signal from the instruction means to changeably place the green filter and the shielding plate in the test window for the first predetermined time and then place the aperture in the test window for the second predetermined time.

4. The optometric apparatus according to claim 1 further including selection means for selecting between a red/green test to be performed by using the green filter and another red/green test to be performed without using the green filter.

5. An optometric apparatus for a subjective examination of a visual function of an eye of an examinee, the apparatus including:
   a pair of right and left lens chamber units, each including,
      a test window; and
      a rotating disk on which a plurality of optical elements are mounted in a circumferential arrangement to be changeably placed in the test window, the optical elements including a green filter and an aperture; and
   control means having a test program including the following steps:
      a first step of placing the green filter in the test window for a first predetermined time while a red optotype and a green optotype are simultaneously presented to the examinee's eye;
      a second step of placing the aperture in the test window after the first step, for a second predetermined time while the red optotype and the green optotype are simultaneously presented to the examinee's eye; and
      a third step of repeating the first and second steps a predetermined number of times.

6. The optometric apparatus according to claim 5, wherein the rotating disk mounts thereon a shielding plate as one of the optical elements, the shielding plate being used for shielding the test window, and
   the first step is to alternately place the green filter and the shielding plate for the first predetermined time.

7. The optometric apparatus according to claim 5, wherein the second predetermined time is set to be shorter than the first predetermined time.

8. The optometric apparatus according to claim 5, wherein the second predetermined time is about 1 second.

9. The optometric apparatus according to claim 5 further including selection means for selecting between a first red/green test to be performed by using the green filter and a second red/green test to be performed without using the green filter, and
   the control means executes the test program when the first red/green test is selected.

* * * * *